(12) United States Patent
Colahan et al.

(10) Patent No.: US 6,946,844 B1
(45) Date of Patent: Sep. 20, 2005

(54) SURFACE AND ABRASIVE TESTING DEVICE

(76) Inventors: Jerry J. Colahan, Mesa, AZ (US); Thomas R. Glover, Scottsdale, AZ (US); Richard Parks, Garrisonville, VA (US)

( * ) Notice: Subject to any disclaimer, the term of this patent is extended or adjusted under 35 U.S.C. 154(b) by 0 days.

(21) Appl. No.: 10/832,898

(22) Filed: Apr. 27, 2004

Related U.S. Application Data

(60) Provisional application No. 60/465,897, filed on Apr. 28, 2003.

(51) Int. Cl.[7] ............................................. G01N 27/02
(52) U.S. Cl. ..................... 324/439; 436/174; 73/49.3
(58) Field of Search ................. 324/438–450, 324/323, 324; 73/49.3, 52; 436/174–178

(56) References Cited

U.S. PATENT DOCUMENTS 4,282,744 A * 8/1981 Dick ........................ 73/49.3

6,159,743 A * 12/2000 Johnson et al. ............. 436/174

* cited by examiner

Primary Examiner—Vincent Q. Nguyen
(74) Attorney, Agent, or Firm—Parsons & Goltry; Robert A. Parsons; Michael W. Goltry

(57) ABSTRACT

A conductivity testing device includes a body containing a magnet positioned to magnetically attach a mounting surface of the body to a surface to be tested. A testing chamber has an opening substantially in a plane with the mounting surface and valves positioned to allow the introducion of a fixed volume of liquid into the chamber. The chamber is sealed to the surface by a tubular resilint seal. An agitating device is mounted in the chamber for agitating liquid introduced into the chamber to wash the enclosed surface area. A testing circuit includes probes positioned in the chamber and a meter for indicating conductivity of a solution contained within the chamber. The testing circuit is electrically coupled to the agitating device in a first mode and connected to the probes in a second mode for testing conductivity of a solution in the chamber.

25 Claims, 4 Drawing Sheets

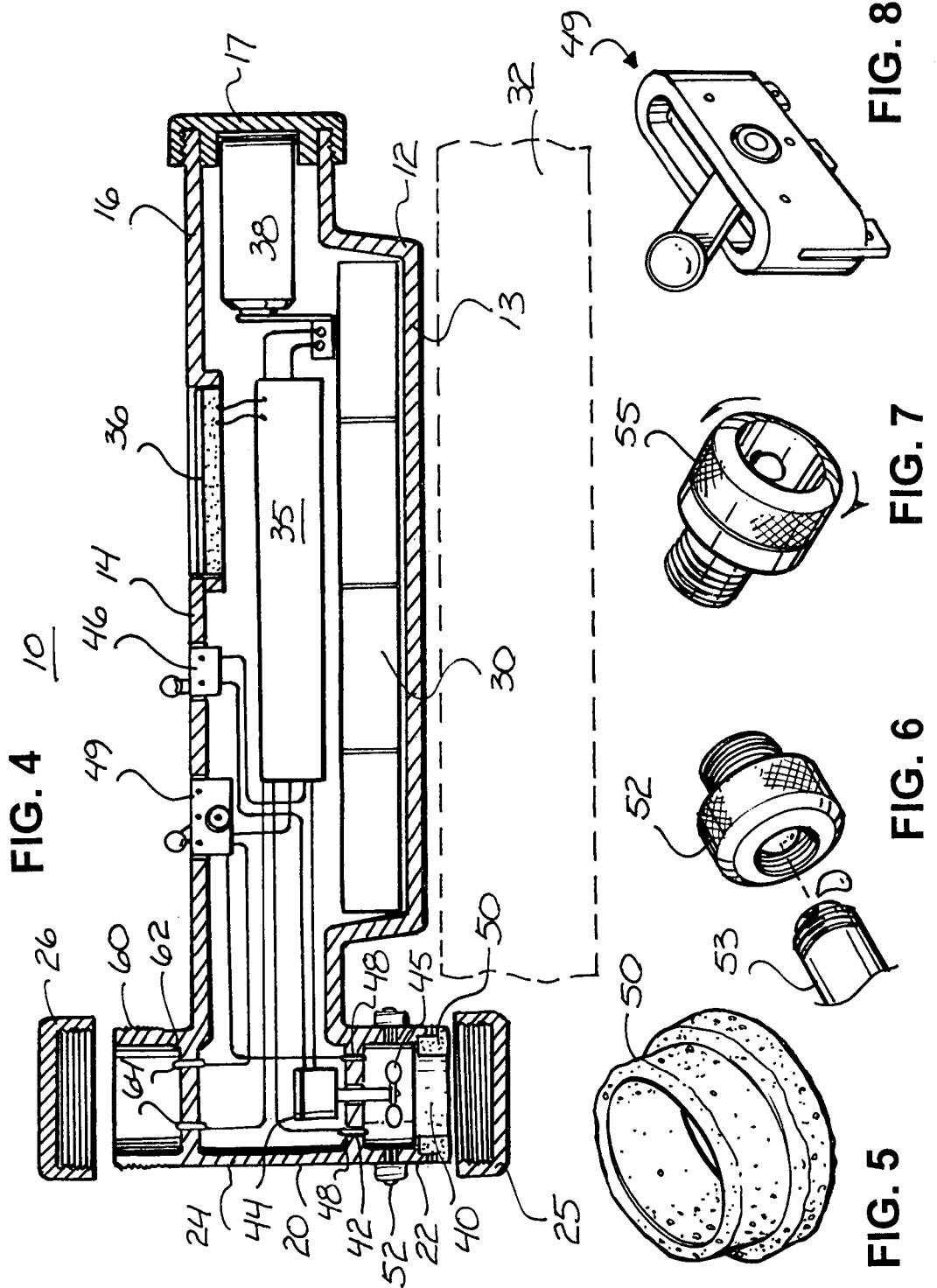

US 6,946,844 B1

SURFACE AND ABRASIVE TESTING DEVICE

CROSS-REFERENCE TO RELATED APPLICATION

This application claims the benefit of U.S. Provisional Application No. 60/465,897, filed 28 Apr. 2003.

FIELD OF THE INVENTION

This invention relates to apparatus and methods for performing various tests on various surfaces.

More particularly, the present invention relates to apparatus and methods for automatically testing surfaces or abrasives for conductivity, pH, and the like.

In a further and more specific aspect, the present invention concerns testing surfaces for salts and the like.

BACKGROUND OF THE INVENTION

In the prior art, the testing of surface salinity can be a complicated and inexact procedure. Generally a conductivity meter is used that includes a sensor cell and samples are prepaired independently. The samples are prepared by washing an exact area of the surface to be tested with an exact quantity of water or other solution. Any deviation in the size of the area or the amount of water or solution will cause substantial deviations in the sample and substantial errors in the test. As understood by those skilled in the art, preparing a sample from different surfaces, e.g. inside surfaces of pipes, outside surfaces of pipes, ceilings, walls, etc., can be challenging. Further, once the sample is prepared the conductivity meter must be zeroed and then the sample must be placed on the testing cell of the meter and the conductivity measured. Clearly, the multiple transfers of the materials making up the sample, from the surface to a container and then to the cell of the meter, can introduce foreign materials that will affect the testing as well as seriously affecting the amount of materials in the sample (especially the water or solution).

It would be highly advantageous, therefore, to remedy the foregoing and other deficiencies inherent in the prior art.

Accordingly, it is an object of the present invention to provide a new and improved testing device and method.

Another object of the present invention is to provide a new and improved testing device and method capable of performing a variety of tests.

And another object of the present invention is to provide a new and improved surface testing device and method capable of performing tests on a variety of surfaces.

Still another object of the present invention is to provide a new and improved testing device and method that is self-contained to include washing, mixing, and testing in a single operation.

Yet another object of the present invention is to provide a new and improved testing device and method in which all of the steps of the test are performed using the single device to eliminate transferring materials between several containers.

SUMMARY OF THE INVENTION

Briefly, to achieve the desired objects of the present invention in accordance with a preferred embodiment thereof, provided is a testing device including a body defining a testing chamber having an opening positioned to be placed against a surface to be tested and a valve for introducing a liquid to the testing chamber. An agitating device is mounted in the testing chamber for agitating liquid introduced into the testing chamber. A seal is positioned in the testing chamber opening for sealing the testing chamber to the surface to be tested. A testing circuit is mounted in the body and includes probes positioned in the testing chamber and a meter coupled to the probes for indicating conductivity of a solution contained within the testing chamber.

In a preferred embodiment, a conductivity testing device includes a body with a mounting surface positioned to be attached to a surface to be tested. A testing chamber has an opening substantially in a plane with the mounting surface and a valve positioned to allow the introducion of a fixed volume of liquid into the chamber. The chamber is sealed to the surface by a tubular resilint seal positioned in the chamber opening. An agitating device is mounted in the chamber for agitating liquid introduced into the chamber to wash a surface area enclosed by the chamber opening. A testing circuit includes probes positioned in the chamber and a meter for indicating conductivity of a solution contained within the chamber. The testing circuit is electrically coupled to the agitating device in a first mode and connected to the probes in a second mode for testing conductivity of a solution in the chamber.

BRIEF DESCRIPTION OF THE DRAWINGS

The foregoing and further and more specific objects and advantages of the invention will become readily apparent to those skilled in the art from the following detailed description of a preferred embodiment thereof, taken in conjunction with the drawings in which:

FIG. 4 is a sectional view of the device of FIG. 1 illustrating internal componenets;

FIG. 5 is an enlarged view in perspective of a seal used in the device of FIG. 1;

FIG. 6 is an enlarged view in perspective of an inlet valve of the device of FIG. 1;

FIG. 7 is an enlarged view in perspective of an outlet valve of the device of FIG. 1;

FIG. 8 is an enlarged view in perspective of a control switch of the device of FIG. 1;

DETAILED DESCRIPTION OF THE DRAWINGS

Figure 1:
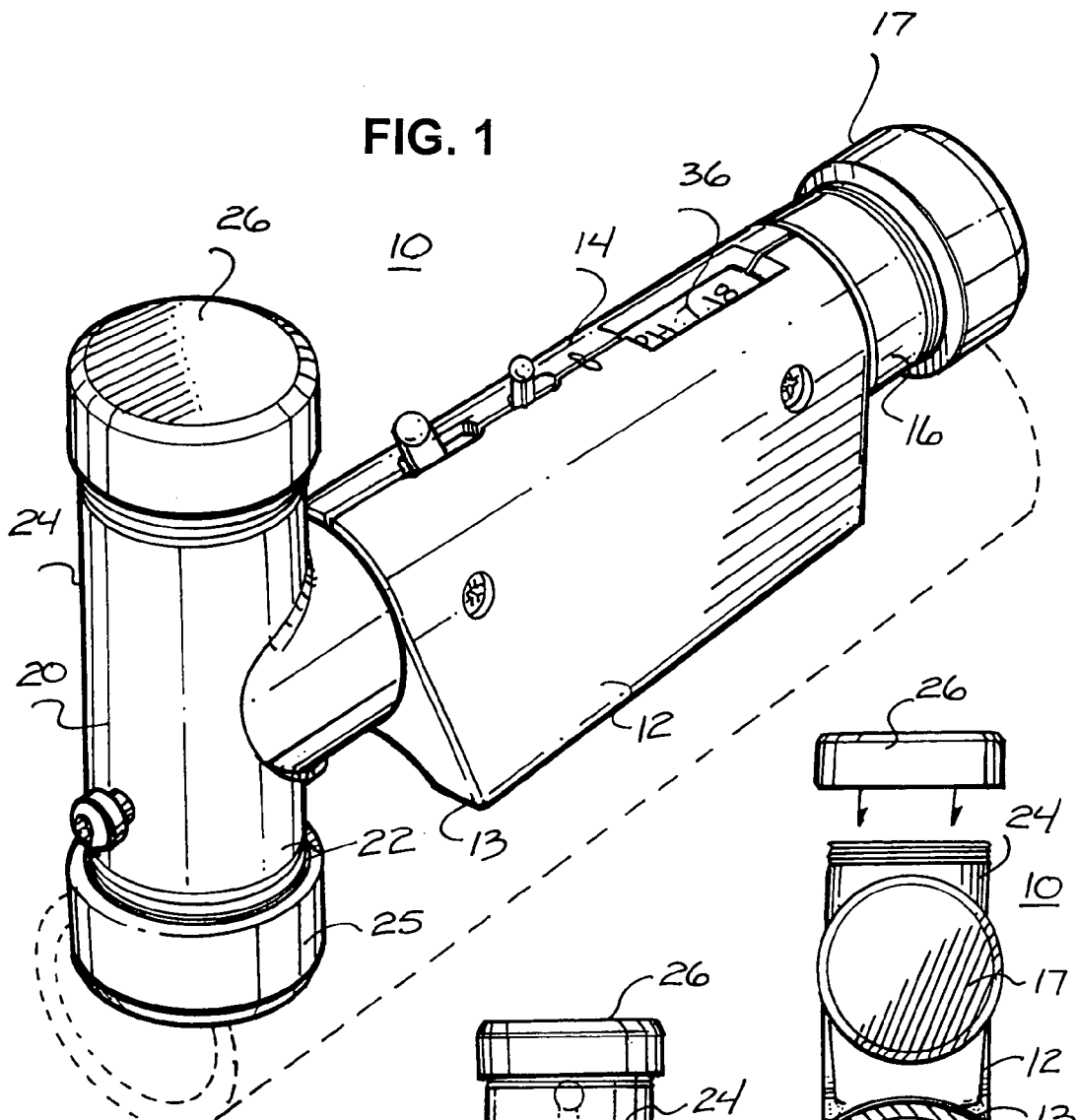
FIG. 1 is a view in perspective of a testing device in accordance with the present invention.
Figure 2:
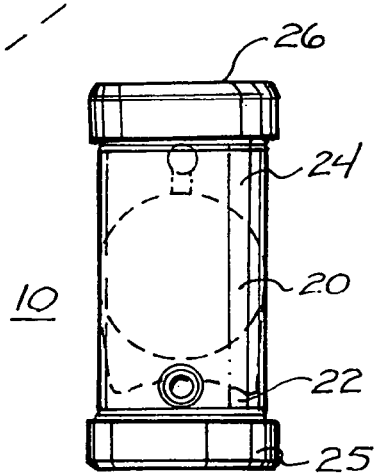
FIG. 2 is a front end view of the device of FIG. 1.
Figure 3:
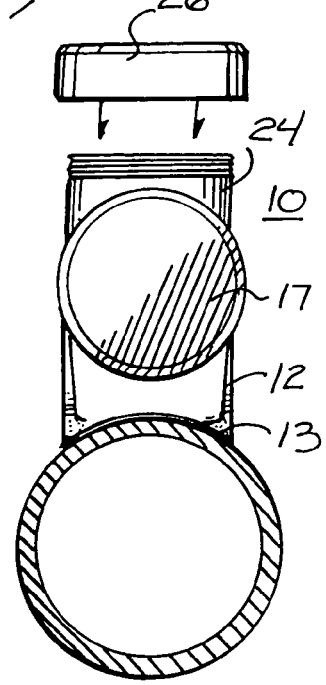
FIG. 3 is a rear end view of the device of FIG. 1.

Turning now to the drawings in which like characters designate similar components throughout the several views, FIGS. 1 and 2 are a view in perspective and a front end view, respectively, of a testing device, generally designated 10, in accordance with the present invention. Device 10 includes a hollow body 12 having a lower surface 13 designed to be attached to a surface to be tested (see also FIG. 3) and an upper surface or control panel 14. A first tubular portion 16 extends rearwardly from hollow body 12 and has a cap 17 threadedly engaged on the rearwardly projectng end for closing portion 16. A T-shaped second tubular portion 20 extends forwardly the front end of hollow body 12 with arms 22 and 24 of the T extending outwardly generally perpendicular to the longitudinal axis of hollow body 12. Arm 22 of portion 20 has a cap 25 threadedly engaged over the open end thereof for sealingly closing arm 22. Also, in this preferred embodiment the open end of arm 22 is positioned generally in a common plane with lower surface 13 of hollow body 12. Arm 24 of portion 20 has a cap 26 threadedly engaged over the open end thereof for sealingly closing arm 24.

Referring additionally to FIG. 4, a magnet or magnets 30 are positioned in hollow body 12 adjacent lower surface 13 so as to magnetically attach device 10 to a surface to be tested, such as the outer diameter of a pipe 32 (shown in broken lines). While other apparatus may be devised to attach device 10 to the surface to be tested, magnets 30 are preferred because of their simplicity, long life, and ease of handling. Also, while the magnet can be an electromagnet, permanent magnets are preferred.

Electrical apparatus 35 is mounted within hollow body 12 and includes testing circuitry for measuring conductivity and pH and also includes automatic zeroing of the testing circuitry as well as temperature compensation. Operation of the testing circuitry will not be described in detail since circuits of this type are commercially available and well known in the art. A meter 36 is either provided on apparatus 35 or electrically attached and positioned to be easily read through a window (see FIG. 1) in control panel 14 of hollow body 12. In this preferred embodiment meter 36 includes a digital readout for simplicity but it will be understood that other readouts may be provided if desired. Power for electrical apparatus 35 is provided by a battery or batteries 38, which are enclosed in tubular portion 16 by cap 17. Cap 17 is threadedly engaged on the rear end of tubular portion 16 so that battery or batteries 38 can be easily changed. As will be understood by those skilled in the art, apparatus 35 can include an automatic indicator (e.g. a reading or light on meter 36) to warn when battery or batteries 38 are low.

A testing chamber 40 is defined by arm 22 of T-shaped tubular portion 20, which has an inner wall 42 separating testing chamber 40 from the remainder of T-shaped tubular portion 20. A dc motor 44 is mounted in T-shaped second tubular portion 20 so that the shaft extends through inner wall 42 and into testing chamber 40. A mixing or agitating device, such as propellor 45, is attached to the shaft so as to rotate with the shaft in testing chamber 40. Motor 44 is electrically connected to battery or batteries 38 through an off/on switch 46, located on control panel 14, and apparatus 35.

A pair of electrical probes 48 are positioned to extend through wall 42 from within the main cavity of tubular portion 20 to within testing chamber 40. One probe of electrical probes 48 is connected directly to apparatus 35 and the second probe is connected through a three position switch 49 to apparatus 35. Referring additionally to FIG. 8, an enlarged view of a typical embodiment for switch 49 is illustrated. Three position switch 49 has a center position in which all power is off and a second position in which power is applied to probes 48 for testing conductivity between probes 48 within testing chamber 40 in apparatus 35.

As explained briefly above, arm 22 of portion 20 has a cap 25 threadedly engaged over the open end thereof for sealingly closing arm 22 during nonuse. With cap 25 removed, a seal 50 is positioned to extend over the edges of the open end. As illustrated in more detail in FIG. 5, seal 50 is formed to fit partially within the open end of arm 22 to hold it in position and to extend over the edges so as to form a seal between the open end of arm 22 and a surface to be tested. Seal 50 is formed of a soft liquid resistant material, such as plastic, rubber, etc. that will resiliantly form and seal to the surface being tested. Further, as explained briefly above, the open end of arm 22 and lower surface 13 of hollow body 12 lie substantially in a common plane. Thus, with cap 25 removed and seal 50 in place, when hollow body 12 is positioned adjacent a surface to be tested it will be held on the surface by magnets 30 and the open end of arm 22 will be sealed on the surface by seal 50, generally as illustrated in FIG. 9.

Typically, the surface area of pipe 32 enclosed within chamber 40 by seal 50 and arm 22 is 10 cm$^2$ and chamber 40 is filled with 10 mL of a selected solution, such as an alkalyn solution or DI water. The selected solution, preferably DI water, is introduced into chamber 40 through an inlet valve 52 in a side wall of arm 22. The solution can be injected using a device such as a hypodermic needle or a device 53 that threads into inlet valve 52 and introduces a measured amount of solution. Further, the volume of DI water or other solution introduced into chamber 40 is controlled by an outlet valve 55, which is positioned in the side wall of arm 22, preferably opposite inlet valve 52 and allows excess fluid to flow out of chamber 40.

Figure 9:
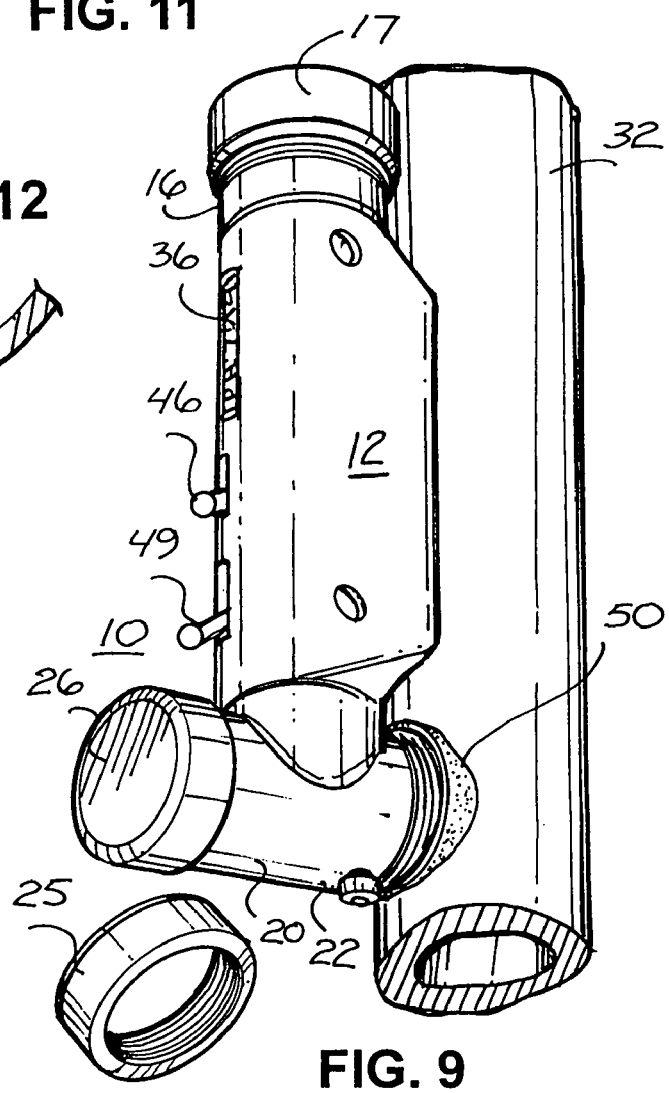
FIG. 9 is a view in perspective of the device of FIG. 1 as applied to the outer diameter of a pipe.

To perform a conductivity test on a surface, such as the outside of pipe 32 in FIG. 9, hollow body 12 is held on pipe 32 by magnets 30 and the open end of arm 22 is sealed on the surface of pipe 32 by seal 50. 10 mL of DI water are introduced into chamber 40 through inlet valve 52. DC motor 44 and propellor 45 are activated, using switch 46, so that the enclosed 10 cm$^2$ surface of pipe 32 within chamber 40 is washed by the DI water and any salt on the surface goes into solution with the DI water. Switch 46 is then turned off and switch 49 is moved to apply power to probes 48 in chamber 40. The conductivity of the solution within chamber 40 appears as a digital readout on meter 36. Since the volume of solution in chamber 40 and the surface area being tested are known, the conductivity can be easily converted into micrograms per square (e.g. cm$^2$) of salt (for example) on the surface of pipe 32. Once the testing is completed device 10 can be disconnected from pipe 32 simply by lifting it away from pipe 10. The seal between chamber 40 and pipe 10 is broken without leaving any adhesive on the surface for later removal.

Referring specifically to FIG. 4, a second conductivity testing chamber 60 is defined by arm 24 of T-shaped tubular portion 20, which has an inner wall 62 separating testing chamber 60 from the remainder of T-shaped tubular portion 20. A pair of electrical probes 64 are positioned to extend through wall 62 from within the main cavity of tubular portion 20 to within testing chamber 60. One probe of electrical probes 64 is connected directly to apparatus 35 and the second probe is connected through three position switch 49 to apparatus 35. Three position switch 49 has the center position in which all power is off and a third position in which power is applied to probes 64 for testing conductivity between probes 64 within testing chamber 60 in apparatus 35.

To operate the second conductivity testing structure, cap 26 is removed from the end of arm 24 so that chamber 60 is open and situated vertically as shown. Material to be tested, such as water or an abrasive in a solution of DI water, is introduced into chamber 60. Switch 49 is then moved to the third position to apply power to probes 64 and a conductivity or pH reading, as selected by the operator, appears on meter 36.

Figure 10:
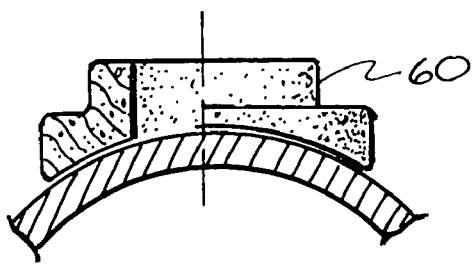
FIG. 10 is an enlarged view of the seal applied to the outer diameter of the pipe.
Figure 11:
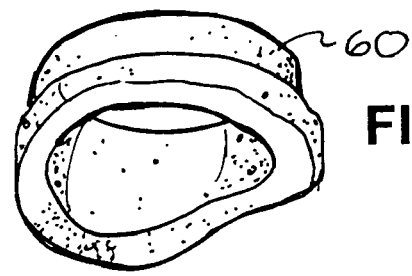
FIG. 11 is a view in perspective of the seal of FIG. 10.
Figure 12:
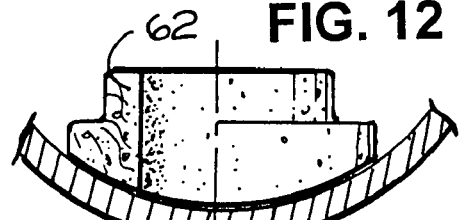
FIG. 12 is an enlarged view of the seal applied to the inner diameter of the pipe.
Figure 13:
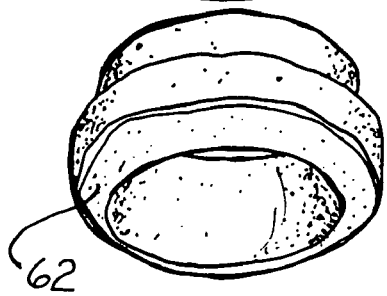
FIG. 13 is a view in perspective of the seal of FIG. 12.
Figure 14:
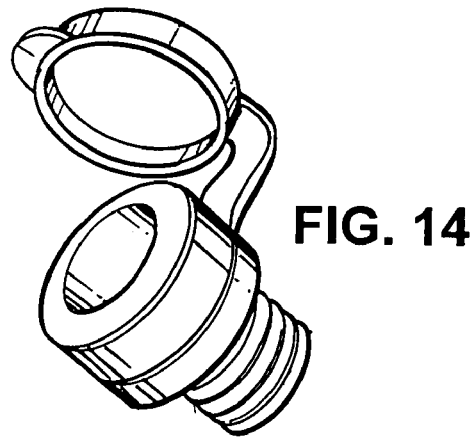
FIG. 14 is an enlarged view in perspective of an inlet/outlet valve.

To make device 10 more useful or adaptable, interchangeable seals are provided, as illustrated in FIGS. 10 through 12. In FIGS. 10 and 11, for example a seal 60 is provided that is shaped to more closely fit the outside diameter of a pipe or other surface with a curved cross-section. In FIGS. 12 and 13, for example a seal 62 is provided that is shaped to more closely fit the inside diameter of a pipe or other surface with a curved cross-section. In addition to or instead of shaped seals, T-shaped tubular portion 20 can be constructed with a changeable end (e.g. providing shorter arms 22 and 24, no arm 24, etc.) so that device 10 can be more easily inserted into pipes and other orfices and used on different sized pipes, inside and outside. Also, either or both inlet and outlet valves can be a simple opening with a cap, as illustrated in FIG. 14.

Figure 15:
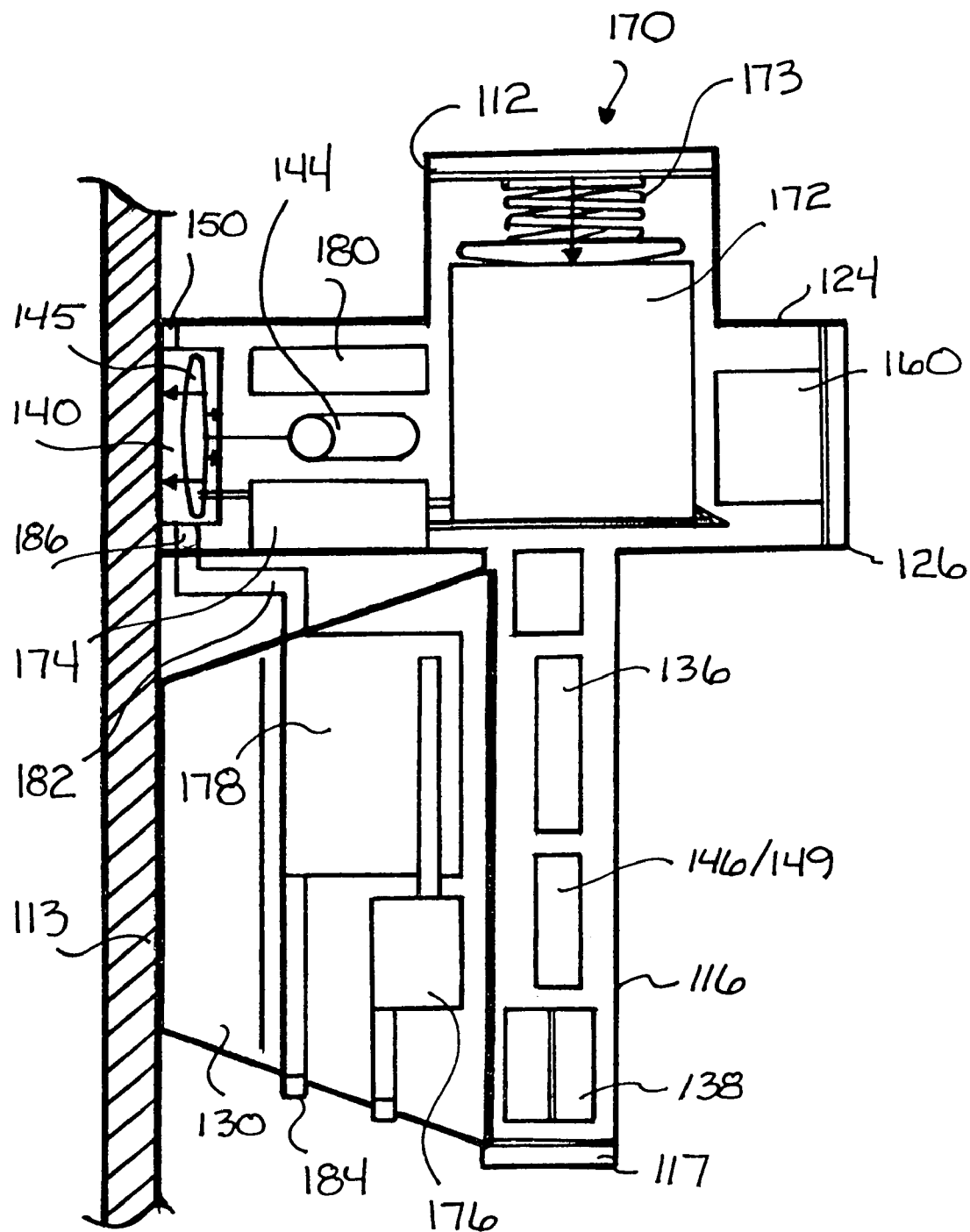
FIG. 15 is a semi-schematic presentation of another embodiment of a testing device in accordance with the present invention.

Turning now to FIG. 15, another embodiment of a testing device, generally designated 100, in accordance with the present invention is illustrated in a semi-schematic presentation. Device 100 is generally similar to device 10 in FIGS. 1 and 4 and components that operate in a similar fashion are designated with similar numbers with '100' added to indicate the different embodiment. Also, components that operate in a fashion similar to components in device 10 will not be discussed in detail.

In device 100, the major difference is in the apparatus for providing a measured amount of solution to testing chamber 140. In device 100, inlet valve 52 and outlet valve 55 have been replaced with apparatus, generally designated 170, for introducing measured amounts of solution to testing chamber 140 a number of times, consecutively. In this embodiment, apparatus 170 includes a solution reservoir 172 with a spring loaded push mechanism 173, a pump 174 coupled to solution reservoir 172 by a conduit and to testing cavity 140, a vacuum pump 176 coupled to a discharge reservoir 178, and a pump control 180.

In this embodiment, solution reservoir 172 includes a flexible bag that is situated within a chamber in hollow body 112. Here it will be understood by those skilled in the art that any of a large variety of liquid containers might be utilized as solution reservoir 172, including structures mounted inside and/or outside hollow body 112. Spring loaded push mechanism 173 is provided to introduce solution with positive pressure to pump 176 to enable testing in all possible positions and for washing the chamber subsequent to a test and/or between tests. Pump 174 is provided for introducing a measured amount of solution to testing chamber 140 for each test. In this preferred embodiment, pump 174 is a specially designed micro annular gear pump utilizing reciprocating and rotary pump action with the ability to accurately meter fluid into testing chamber 140 with a volumetric efficiency precision nearing 100%. Micro pump 174 operates with an actuator equipped with an electric motor controlled by pump control 180, which may also control vacuum pump 176. The amount of fluid introduced into testing chamber 149 can be adjusted depending on the amount needed. In essence, micro pump 174 can be considered either as an inlet valve or as including an inlet valve. Discharge reservoir 178 is connected to testing chamber 140 by a conduit, or vacuum line, 182 and is also provided with a waste solution dumping conduit 184. A check valve 186 holds fluid in testing chamber 140 until sufficient pressure is removed by vacuum pump 176.

In operation, device 100 is provided with a reservoir 172 containing sufficient solution to perform a number of test, e.g. surface soluble salt tests. Testing chamber 140 is initially cleaned by pressing spring loaded push mechanism 173 to introduce solution therein. The solution is agitated and immediately removed to discharge reservoir 178 by activating vacuum pump 176. Device 100 is then, preferably, attached to a surface to be tested using magnets 130, or it can be attached by other apparatus, or even simply held in place by hand.

With testing chamber 140 sealed to a surface to be tested, pump control 180 is used to activate pump 174 to introduce an accurately measured amount of testing solution from reservoir 172 to testing chamber 140. Motor 144 is activated to cause agitating device 145 to wash the enclosed surface to be tested with the accurately metered solution. Conductivity, in this specific example, is then displayed on digital readout meter 136. Vacuum pump 176 is then activated to remove used solution from testing chamber 140 and push mechanism 173 can be used to flush chamber 140 clean for the next operation. Used fluid can be discharged from discharge reservoir 178 when desired by positioning device 100 in a vertical position. In this fashion a number of tests can be easily performed consecutively in a short time without the need to introduce new solution for each test.

Thus, a new and improved testing device and method are desclosed that are capable of performing a variety of tests on a variety of surfaces, e.g. inside and outside pipes, flat steel, ships hulls, tanks and the like. Further, the device is highly versatile and can be used for testing surfaces, abrasives, water, etc. Also, the new and improved testing device is self-contained to include washing, mixing, and testing in a single operation, which greatly improves the accuracy of the test results and all of the steps of the test are performed using the single device to eliminate transferring materials between several containers, which reduces mistakes.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A testing device comprising:
    a body defining a testing chamber having an opening positioned to be placed against a surface to be tested and a valve for introducing a liquid to the testing chamber, an agitating device mounted in the testing chamber for agitating liquid introduced into the testing chamber;
    a seal positioned in the testing chamber opening for sealing the testing chamber to the surface to be tested; and
    a testing circuit mounted in the body and including probes positioned in the testing chamber and a meter coupled to the probes for indicating conductivity of a solution contained within the testing chamber.

2. A testing device as claimed in claim 1 wherein the body is constructed to be attached to the surface to be tested and the opening of the testing chamber is positioned to but against the surface to be tested with the body attached.

3. A testing device as claimed in claim 1 further including a reservoir coupled through the valve to the testing chamber and wherein the valve includes a pump for metering a precise amount of solution into the testing chamber.

4. A testing device as claimed in claim 3 wherein the reservoir has a capacity sufficient to perform a plurality of tests consecutively and to flush the testing chamber between tests.

5. A testing device comprising:
   a body having a mounting surface attachable to a surface to be tested;
   a testing chamber having an opening substantially in a plane with the mounting surface and a valve for introducing a liquid to the testing chamber, an agitating device mounted in the testing chamber for agitating liquid introduced into the testing chamber; and
   a testing circuit including probes positioned in the testing chamber and a meter coupled to the probes for indicating conductivity of a solution contained within the testing chamber.

6. A testing device as claimed in claim 5 wherein the body further includes magnets positioned to magnetically attach the mounting surface of the device to the surface to be tested.

7. A testing device as claimed in claim 5 further including a seal positioned in the testing chamber opening for sealing the testing chamber to the surface to be tested with the mounting surface attached to the surface to be tested.

8. A testing device as claimed in claim 7 wherein the seal includes a soft liquid resistant material formed to be positioned between edges of the testing chamber opening and the surface to be tested.

9. A testing device as claimed in claim 8 wherein at least one of the testing chamber, the testing chamber opening, and the seal are changeable to fit different sizes of an inside surface of a pipe and an outside surface of a pipe.

10. A testing device as claimed in claim 5 wherein the body further includes a second testing chamber with probes positioned in the second testing chamber and electrically attached to the testing circuit and the meter for indicating conductivity of a solution contained within the second testing chamber.

11. A testing device as claimed in claim 10 wherein the testing chamber and the second testing chamber are formed in opposite arms of a common T-shaped tubular body.

12. A testing device as claimed in claim 5 further including a reservoir coupled through the valve to the testing chamber and wherein the valve includes a pump for metering a precise amount of solution into the testing chamber.

13. A testing device as claimed in claim 12 wherein the reservoir has a capacity sufficient to perform a plurality of tests consecutively and to flush the testing chamber between tests.

14. A testing device comprising:
   a body including a magnet and having a mounting surface magnetically attachable by the magnet to a surface to be tested;
   a testing chamber having an opening substantially in a plane with the mounting surface and inlet and outlet valves positioned to allow the introducion of a fixed volume of liquid to the testing chamber, an agitating device mounted in the testing chamber for agitating liquid introduced into the testing chamber; and
   a testing circuit including probes positioned in the testing chamber and a meter for indicating conductivity of a solution contained within the testing chamber, the testing circuit being electrically coupled to the agitating device in a first mode for activating the agitating device and connected to the probes in a second mode for testing conductivity of a solution in the testing chamnber.

15. A testing device as claimed in claim 14 wherein the magnet positioned to magnetically attach the mounting surface of the device to the surface to be tested includes a permanent magnet.

16. A testing device as claimed in claim 14 further including a seal positioned in the testing chamber opening for sealing the testing chamber to the surface to be tested with the mounting surface attached to the surface to be tested.

17. A testing device as claimed in claim 16 wherein the seal includes a soft liquid resistant material formed to be positioned between edges of the testing chamber opening and the surface to be tested.

18. A testing device as claimed in claim 14 wherein the body further includes a second testing chamber with probes positioned in the second testing chamber and electrically attached to the testing circuit and the meter for indicating conductivity of a solution contained within the second testing chamber.

19. A testing device as claimed in claim 18 wherein the testing chamber and the second testing chamber are formed in opposite arms of a common T-shaped tubular body.

20. A testing device as claimed in claim 14 further including a reservoir coupled through the valves to the testing chamber and wherein the valves include a pump for metering a precise amount of solution into the testing chamber.

21. A testing device as claimed in claim 20 wherein the reservoir has a capacity sufficient to perform a plurality of tests consecutively and to flush the testing chamber between tests.

22. A method of testing surface materials by testing the conductivity comprising the steps of:
   providing a device including a body having a mounting surface attachable to a surface to be tested, a testing chamber having an opening substantially in a plane with the mounting surface and a valve for introducing a fixed volume of liquid to the testing chamber, an agitating device mounted in the testing chamber for agitating liquid introduced into the testing chamber, and a testing circuit including probes positioned in the testing chamber and a meter for indicating conductivity of a solution contained within the testing chamber, the testing circuit being electrically coupled to the agitating device in a first mode for activating the agitating device and connected to the probes in a second mode for testing conductivity of a solution in the testing chamnber;
   mounting the body of the device with the mounting surface attached to the surface to be tested and sealing the opening of the testing chamber to the surface to be tested so that a fixed area of the surface to be tested is included in the opening of the testing chamber;
   introducing a fixed volume of liquid into the testing chamber through the valve;
   activating the agitating device so that the fixed volume of liquid in the testing chamber washes any material from the fixed area of the surface to be tested included in the opening of the testing chamber and incorporates it into a solution with the fixed volume of liquid in the testing chamber; and
   electrically coupling the probes to the testing circuit and the meter so as test the conductivity of the solution in the testing chamber.

23. A method of testing surface materials by testing the conductivity as claimed in claim 22 wherein the step of sealing the opening of the testing chamber to the surface to be tested includes providing a soft liquid resistant tubular seal positioned in the testing chamber opening between edges of the testing chamber opening and the surface to be tested.

24. A method of testing surface materials by testing the conductivity as claimed in claim 22 wherein the step of providing a device includes providing a device having a second testing chamber with a second pair of probes positioned in the second testing chamber and electrically attached to the testing circuit and the meter and the method further includes steps of introducing a solution to be tested to the second testing chamber, and electrically coupling the second probes to the testing circuit and the meter so as test the conductivity of the solution in the second testing chamber.

25. A method of testing surface materials by testing the conductivity as claimed in claim 22 wherein the step of providing a device including a body further includes providing a solution reservoir within the body and in communication with the valve and the valve includes a pump for metering a precise amount of solution into the testing chamber, and the step of introducing a fixed volume of liquid into the testing chamber through the valve includes activating the pump.

* * * * *